US00PP32359P3

(12) United States Plant Patent
Hansen

(10) Patent No.: US PP32,359 P3
(45) Date of Patent: Oct. 20, 2020

(54) *VERONICA* PLANT NAMED 'LAVENDER LIGHTSABER'

(50) Latin Name: ***Veronica spicata* L.**
Varietal Denomination: Lavender Lightsaber

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 71 days.

(21) Appl. No.: 16/350,941

(22) Filed: Feb. 1, 2019

(65) Prior Publication Data

US 2020/0253104 P1 Aug. 6, 2020

(51) Int. Cl.
*A01H 6/68* (2018.01)
*A01H 6/00* (2018.01)
*A01H 5/02* (2018.01)

(52) U.S. Cl.
USPC ..... Plt./251
CPC ..... *A01H 6/00* (2018.05); *A01H 5/02* (2013.01)

(58) Field of Classification Search
USPC ..... Plt./251
CPC ..... A01H 6/68; A01H 5/02
See application file for complete search history.

*Primary Examiner* — Keith O. Robinson

(57) ABSTRACT

The new and distinct cultivar of ornamental spike speedwell plant, *Veronica spicata* 'Lavender Lightsaber', with upright narrow habit, stiff, upright, freely-branched spikes producing soft lavender flowers beginning in late spring and continuing for up to eight weeks. The new plant is useful in the landscape as a specimen, en masse, as a container plant or as a cut flower.

1 Drawing Sheet

Botanical classification: *Veronica spicata* L.
Variety denomination: 'Lavender Lightsaber'.

STATEMENT REGARDING PRIOR DISCLOSURES UNDER 37 CFR 1.77(B)(6)

The first public disclosure of the claimed plant, in the form of a photograph and brief description on a website operated by Walters Gardens, Inc. was on Feb. 1, 2018. The claimed plant was first sold on Jul. 9, 2018 by Walters Gardens, Inc., who obtained the plant and all information relating thereto, from the inventor. No plants of *Veronica* 'Lavender Lightsaber' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct cultivar of spike speedwell, botanically known as *Veronica spicata* 'Lavender Lightsaber', and hereinafter referred to as the cultivar 'Lavender Lightsaber' or the "new plant". The new plant was an insect pollination controlled by the inventor in the summer of 2013 in the hybridizing greenhouses of a wholesale perennial nursery in Zeeland, Mich., USA, with *Veronica* 'Red Fox' (not patented) as the female parent and the unreleased proprietary hybrid known only as 08-13-01 (not patented) as the male parent.

The new plant has been asexually propagated initially by division and later by basal cuttings and shoot tip tissue culture at the same nursery in the greenhouses in Zeeland, Mich., since the summer of 2015 with subsequent asexually propagated plants found to be identical to the original selection with all the same traits as the original seedling.

BRIEF SUMMARY OF THE PLANT

*Veronica* 'Lavender Lightsaber' is unique from all other spike speedwell known to the inventor. Several other cultivars may have some similar traits, but this is the only variety known by the inventor to have the following characteristic combinations that establish the new plant as unique:

1. Upright, narrow habit with stiff, tall, upright spikes above dense stems of medium green foliage.
2. Scapes with numerous flowers of soft lavender petals.
3. Freely-branched peduncles with long blooming season.

The closest comparison varieties known to the inventor are 'Blue Skywalker' U.S. Plant Pat. No. 29,406, 'Eveline' U.S. Plant Pat. No. 14,888, 'Perfectly Picasso' U.S. Plant Pat. No. 29,720, 'Alllove' U.S. Plant Pat. No. 21,478, 'Sweet Lullaby' U.S. Plant Pat. No. 23,611, 'Blue Skywalker' has a more bluish flower of similar height. 'Eveline' has deeper purplish-red flowers on smaller plants. 'Sweet Lullaby' has flowers that are slightly deeper lavender on much shorter stems. The flowers of 'Alllove' are intense red purple and the habit is much shorter than the new plant. 'Red Fox' has flowers that are bright fuchsia pink and the habit is shorter and less spreading. 'Perfectly Picasso' has flowers that are medium pink and the habit is broader and more rounded. The male parent 08-13-01 was taller and has flowers of soft lavender color.

BRIEF DESCRIPTION OF THE DRAWINGS

The photographs of the new plant demonstrate the overall appearance and unique traits of 'Lavender Lightsaber' as a three-year-old plant grown in a full-sun trial garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
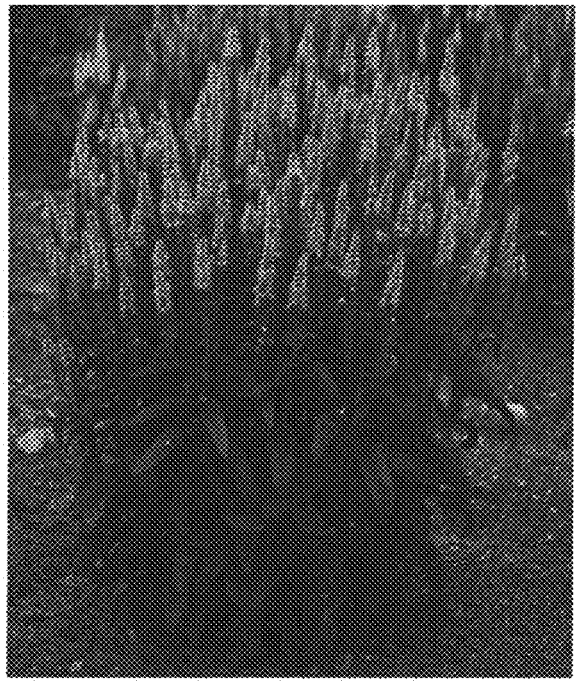
FIG. 1 shows the plant in full flower.
Figure 2:
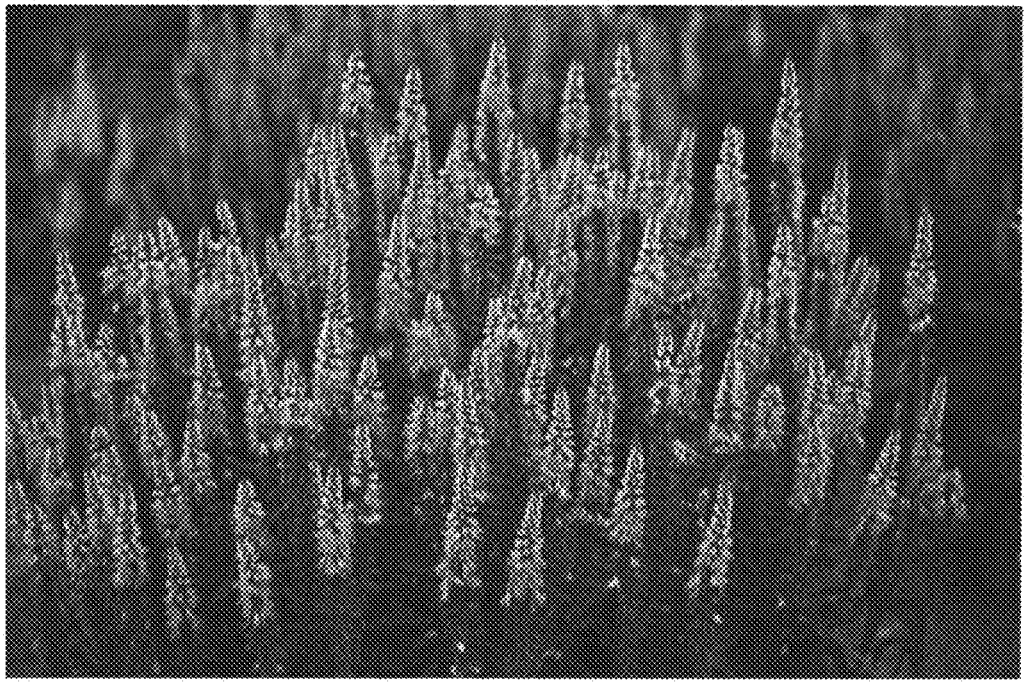
FIG. 2 shows a close-up of the flowers and buds.

The following descriptions and color references of *Veronica* 'Lavender Lightsaber' are based on the 2015 edition of The Royal Horticultural Society Colour Chart except where common dictionary terms are used. 'Lavender Lightsaber' has not been observed under all possible environments. The phenotype may vary slightly with different growing environments such as temperature, light, fertility, soil pH, moisture and maturity levels, but without any change in the genotype. The following observations and size descriptions are based on three-year-old and one-year-old plants grown in a full-sun trial garden of a nursery in Zeeland, Mich. with supplemental fertilizer and water as needed.

Botanical classification: *Veronica spicata;*

Parentage: 'Red Fox' as the female (seed parent); the proprietary hybrid known as 08-13-01 as the male (pollen parent);

Propagation: The plant roots from cuttings in about 2 weeks and finishes to flowering in a 3.8 liter container in 8 to 10 weeks following a vernalization period of about 8 weeks;

Roots: Fibrous; heavily branching; color between RHS 158A and RHS 161D;

Plant habit: Hardy herbaceous perennial, compact, with average 45 stems, main stems to about 75 cm tall and clumping to about 45 cm wide; flowering beginning late spring in Michigan and continuing for up to 8 weeks;

Leaves: Simple, flat, lanceolate, opposite, serrated with about 2.5 teeth per centimeter; micro-puberulent abaxial and adaxial, lustrous adaxial and matte abaxial; acute apex; distal leaves with attenuate base and proximal leaves with rounded base; about 10.5 cm long by 3.0 cm wide, average about 8.0 cm long and 2.2 cm wide, decreasing in both length and width distally; about 16 leaves per stem;

Leaf color: Mature adaxial between RHS 139A and RHS 137A, abaxial nearest RHS 137B; young expanding adaxial between RHS 146A and RHS 146B, abaxial nearest RHS 146B;

Veins: Pinnate, abaxial midrib costate; puberulent abaxial and glabrate to glabrous adaxial;

Vein color: Adaxial midrib nearest RHS 138B and lateral veins nearest RHS 137A; abaxial midrib nearest RHS 145A and lateral veins nearest RHS 137B;

Petiole: Simple, puberulent abaxial and adaxial; margin ciliolate; to about 10.0 mm long and 4.0 mm wide decreasing distally to an average about 3.0 mm long and 3.5 mm wide;

Petiole color: Adaxial between RHS NN137A and RHS 139A; abaxial nearest RHS 137B;

Stem: Terete; puberulent; length about 30 cm before flowers, diameter about 4.0 mm at base; color nearest RHS 138B;

Internodes: 7 below flowers; about 4.3 cm apart; color nearest RHS 157C;

Inflorescence: Heavily branched upright spikes in compressed conglomerate; about 40 cm long and 8.5 cm wide; with about 350 flowers per center stem, 150 flowers per branch and about 650 per branched peduncle;

Flower bud two days prior to opening: Convolute; oblong; rounded base and apex; glabrous; about 8.0 mm long and 3.0 mm diameter;

Flower bud color: One to two days prior to opening blend between RHS N82C and RHS N82D;

Flowers: Zygomorphic, perfect, complete; about 10.0 mm wide and about 12.0 mm long to exserted anthers; corolla about 10.0 mm across and about 8.0 mm long; corolla tube fused in basal 2.0 mm and 1.3 mm diameter; flowers persist individually for 4 to 6 days whether on the plant or cut; petals self-cleaning, sepals persistent; attitude outwardly;

Flower fragrance: Not detectible;

Flower timing: Late spring and continuing for about eight weeks;

Petals: Four; one larger petal above and two on either side, one slightly small below; rounded apices; entire margin; glabrous adaxial and abaxial except basal 2.0 mm adaxial of fused tube pubescent tuft; fused in basal 2.0 mm; larger top and side petals about 8.0 mm long by 4.0 mm wide, smaller lower petal about 8.0 mm long and 3.0 mm wide;

Petal color: Abaxial and adaxial nearest RHS N81C with corolla tube base lightening RHS NN155D; adaxial tuft of hairs nearest RHS NN155D;

Androecium:

*Filaments*.—Two; divergent; glabrous; epipetalous about 1.0 mm from base; about 9.0 mm long by 0.3 mm; color nearest RHS N78C distally becoming white, RHS NN155D proximally.

*Anther*.—Dorsifixed, longitudinal; ellipsoidal, with acute apex and rounded base; about 2.5 mm long by 1.0 mm wide; color nearest between RHS 186C and RHS 186D adaxial and nearest RHS N75A abaxial.

*Pollen*.—Abundant, globose, less than 0.1 mm; nearest RHS 10C.

Gynoecium: One, superior; exserted; persists after petal drop;

*Style*.—Cylindrical; curved upwards; attitude mostly outwardly; about 7.0 mm long by 0.5 mm wide; color nearest RHS N78C.

*Stigma*.—Globose; about 0.3 mm in diameter; color RHS 77A.

*Ovary*.—Globose to ellipsoid; about 1.0 mm long and 1.0 mm across; color nearest RHS 145B.

Calyx: Campanulate; 3.0 mm long and 3.0 mm diameter;

Sepals: Four; two larger and two smaller; lanceolate; adaxial dull, glabrous; abaxial microscopically puberulent; acute apex; basal 1.5 mm fused forming campanulate calyx; margin entire, ciliolate; larger pair about 3.0 mm long and 1.0 mm wide; smaller pair about 2.5 mm long and 1.0 mm wide;

Sepal color: Abaxial and adaxial nearest RHS 138A;

Peduncle: About 70 per plant; raceme, strong, virgate, freely branched at nodes; cylindrical; minutely pubescent to canescent; flowering portion to about 40.0 cm long and about 8.5 cm across with stem base diameter about 3.5 mm; freely branching at nearly every node;

Peduncle color: Nearest RHS 146C;

Pedicel: Rigid; cylindrical, puberulent; about 1.5 mm long and 0.5 mm wide, attitude semi-upright;

Pedicel color: Nearest RHS 146A;

Bract: One, subtending each flower, linear, acute apex, mostly entire margin, sessile, based fused to peduncle, proximal bracts about 2.2 cm long and 4.0 mm wide and decreasing distally to about 4.0 mm long and less than 1.0 mm wide;

Bract color: Nearest RHS 146C both adaxial and abaxial;

Fruit: Ellipsoid with rounded apex and base, about 3.1 mm long and 2.5 mm across; color between RHS 165A and RHS 165B;

Hardiness, pest and disease resistance: The new plant grows best with plenty of moisture and adequate drainage, but is able to tolerate some drought when mature. Hardiness at least from USDA zone 4 through 9. Disease and pest resistance beyond what is typical of that of other spike speedwell has not been observed, including powdery mildew (*Podosphaera xanthii*), rust (*Puccinia veronicae-longifoliae*), and browsing from rabbits (*Oryctolagus cuniculus*), and deer (*Odocoileus virginianus*).

I claim:

1. A new and distinct cultivar of ornamental Spike Speedwell plant, *Veronica spicata* 'Lavender Lightsaber', as herein described and illustrated.

* * * * *